US012115388B2

(12) United States Patent
Tang et al.

(10) Patent No.: US 12,115,388 B2
(45) Date of Patent: Oct. 15, 2024

(54) JAW ASSEMBLY AND MEDICAL ACCELERATOR

(71) Applicants: OUR UNITED CORPORATION, Xi'an (CN); OUR Innobeam Medical Co., Ltd, Beijing (CN)

(72) Inventors: Ziming Tang, Xi'an (CN); Hongbin Zhao, Xi'an (CN); Junfeng Li, Xi'an (CN)

(73) Assignees: OUR UNITED CORPORATION (CN); OUR Innobeam Medical Co., Ltd (CN)

( * ) Notice: Subject to any disclaimer, the term of this patent is extended or adjusted under 35 U.S.C. 154(b) by 925 days.

(21) Appl. No.: 17/168,967

(22) Filed: Feb. 5, 2021

(65) Prior Publication Data

US 2021/0330991 A1  Oct. 28, 2021

(30) Foreign Application Priority Data

Apr. 26, 2020  (CN) .......................... 202020661351.8

(51) Int. Cl.
*A61N 5/10* (2006.01)
*G21K 1/02* (2006.01)

(52) U.S. Cl.
CPC ............. *A61N 5/1042* (2013.01); *G21K 1/02* (2013.01)

(58) Field of Classification Search
None
See application file for complete search history.

(56) References Cited

U.S. PATENT DOCUMENTS 5,332,908 A *  7/1994  Weidlich .............. A61N 5/1042
378/65
2014/0146949 A1 *  5/2014  Pan .......................... A61B 6/06
378/152

* cited by examiner

*Primary Examiner* — Hoon K Song
(74) *Attorney, Agent, or Firm* — Emerson, Thomson & Bennett, LLC; Roger D. Emerson; Matt J. Wilson

(57) ABSTRACT

A jaw assembly and a medical accelerator are provided. The jaw assembly includes: a jaw base, a moving assembly and at least one set of jaws, each set of jaws including at least two jaw bodies. The jaw base is detachably connected to a mounting seat of a treatment head beam shaping module of a medical accelerator, and when the jaw base is mounted on the mounting seat, a beam opening formed is located under the treatment head beam shaping module. The jaw body is connected to the jaw base through the moving assembly, and the moving assembly is configured to move the jaw body to between the beam opening and the treatment head beam shaping module, or to move the jaw body out between the beam opening and the treatment head beam shaping module to adjust a beam flow through the beam opening.

17 Claims, 12 Drawing Sheets

JAW ASSEMBLY AND MEDICAL ACCELERATOR

CROSS-REFERENCE TO RELATED APPLICATIONS

The present application claims priority to Chinese application No. 202020661351.8 filed on Apr. 26, 2020 and entitled "JAW ASSEMBLY AND MEDICAL ACCELERATOR", which is hereby incorporated by reference in its entireties.

TECHNICAL FIELD

Embodiments of the present disclosure relate to the technical field of medical equipment, and in particular to a jaw assembly and a medical accelerator.

BACKGROUND

Radiation therapy is a method for treating a malignant tumor by using radiation rays to completely necrosis or apoptosis of cancer cells. Medical accelerators are commonly used in radiation therapy as equipment for implementing radiation therapy.

Typically, a medical accelerator includes a treatment head beam shaping module for forming a radiation beam and a jaw, and the jaw may be configured to assist the treatment head beam shaping module to form a radiation field.

SUMMARY

A jaw is usually directly connected to a mounting frame of a treatment head beam shaping module, and is integrated with the mounting frame. When the jaw fails, it is necessary to remove the jaw from the mounting frame to separate the jaw from a medical accelerator for maintenance, which increases a maintenance difficulty of the medical accelerator and impairs user experience.

In view of this, embodiments of the present utility model provide a jaw assembly and a medical accelerator to overcome all or part of the technical defects in the prior art.

An embodiment of the present disclosure provides a jaw assembly, including: a jaw base, a moving assembly and at least one set of jaws, each set of jaws including at least two jaw bodies. The jaw base is detachably connected to a mounting seat of a treatment head beam shaping module of a medical accelerator, and when the jaw base is mounted on the mounting seat, a beam opening formed is located under the treatment head beam shaping module. The jaw body is connected to the jaw base through the moving assembly, and the moving assembly is configured to move the jaw body to between the beam opening and the treatment head beam shaping module, or to move the jaw body out between the beam opening and the treatment head beam shaping module to adjust a beam flow through the beam opening.

An embodiment of the present disclosure further provides a medical accelerator, including a mounting seat and the jaw assembly of any one of the above.

In the embodiments of the present disclosure, the provided jaw assembly includes a jaw base, a moving assembly and at least one set of jaws, each set of jaws including at least two jaw bodies. The jaw base is detachably connected to a mounting seat of a treatment head beam shaping module of a medical accelerator, and when the jaw base is mounted on the mounting seat, a beam opening formed is located under the treatment head beam shaping module. The jaw body is connected to the jaw base through the moving assembly, and the moving assembly is configured to move the jaw body to between the beam opening and the treatment head beam shaping module, or to move the jaw body out between the beam opening and the treatment head beam shaping module to adjust a beam flow through the beam opening. In the above solution, by removing the jaw base from the mounting seat of the treatment head beam shaping module of the medical accelerator, the jaw in the jaw assembly may be conveniently maintained. Therefore, the solution reduces the maintenance difficulty of the medical accelerator, and improves the user experience.

BRIEF DESCRIPTION OF THE DRAWINGS

Hereinafter, some specific embodiments of the embodiments of the present disclosure will be described in detail in an exemplary but not restrictive method with reference to the accompanying drawings. The same reference numerals in the accompanying drawings indicate the same or similar components or parts. Those skilled in the art should understand that these accompanying drawings are not necessarily drawn by ratio. In the accompanying drawings.

DETAILED DESCRIPTION OF EMBODIMENTS

The specific implementation of embodiments of the present utility model will be further described below in conjunction with the accompanying drawings of the embodiments of the present utility model.

Embodiment 1

Figure 1:
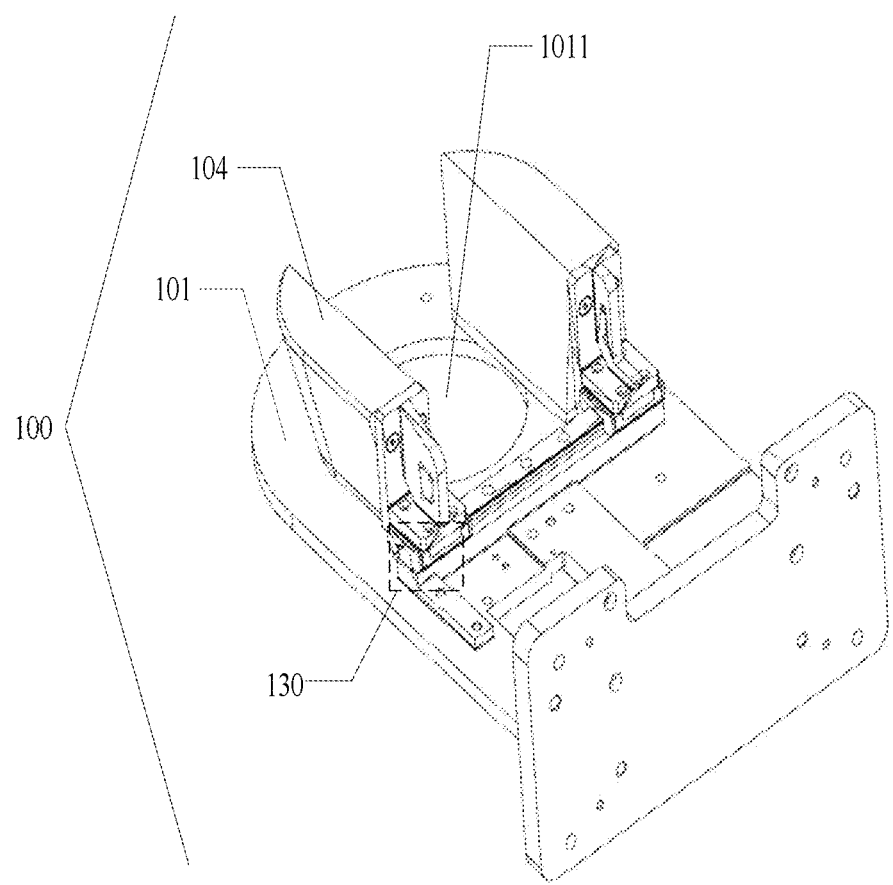
FIG. 1 is a schematic structural diagram of a jaw assembly provided by an embodiment of the present disclosure.

Embodiment 1 of the present disclosure provides a jaw assembly, as shown in FIG. 1. FIG. 1 is a schematic structural diagram of a jaw assembly provided by an embodiment of the present disclosure. The jaw assembly 100 includes: a jaw base 101, a moving assembly 130 and at least one set of jaws, each set of jaws including at least two jaw bodies 104.

The jaw base 101 is detachably connected to a mounting seat of a treatment head beam shaping module of a medical accelerator, and when the jaw base 101 is mounted on the mounting seat, a beam opening 1011 formed is located under the treatment head beam shaping module.

The jaw body 104 is connected to the jaw base 101 through the moving assembly 130, and the moving assembly 130 is configured to move the jaw body 104 to between the beam opening 1011 and the treatment head beam shaping module, or to move the jaw body 104 out between the beam opening 1011 and the treatment head beam shaping module to adjust a beam flow through the beam opening 1011.

A shape of the beam opening may be rectangular or other shapes. The embodiments of the present disclosure do not limit the shape of the beam opening. For ease of understanding, the shape of the beam opening in the embodiments of the present disclosure is a rectangle with curved corners as an example for description.

In the embodiments of the present disclosure, by removing the jaw base from the mounting seat of the treatment head beam shaping module of the medical accelerator, the jaw in the jaw assembly may be conveniently maintained. Therefore, the solution reduces the maintenance difficulty of the medical accelerator, and improves the user experience.

Alternatively, in order to facilitate the maintenance of the treatment head beam shaping module, the jaw base may further include a connecting portion adapted to be detachably connected to the mounting seat of the treatment head beam shaping module, to facilitate separation of the mounting seat of the treatment head beam shaping module from the jaw base.

Alternatively, the connecting portion may include a first sliding mechanism mounted on a surface of the jaw base corresponding to the mounting seat, the first sliding mechanism cooperates with a second sliding mechanism on the mounting seat such that separation and mounting between the jaw assembly and the mounting seat are implemented through a relative movement between the first sliding mechanism and the second sliding mechanism.

Figure 12:
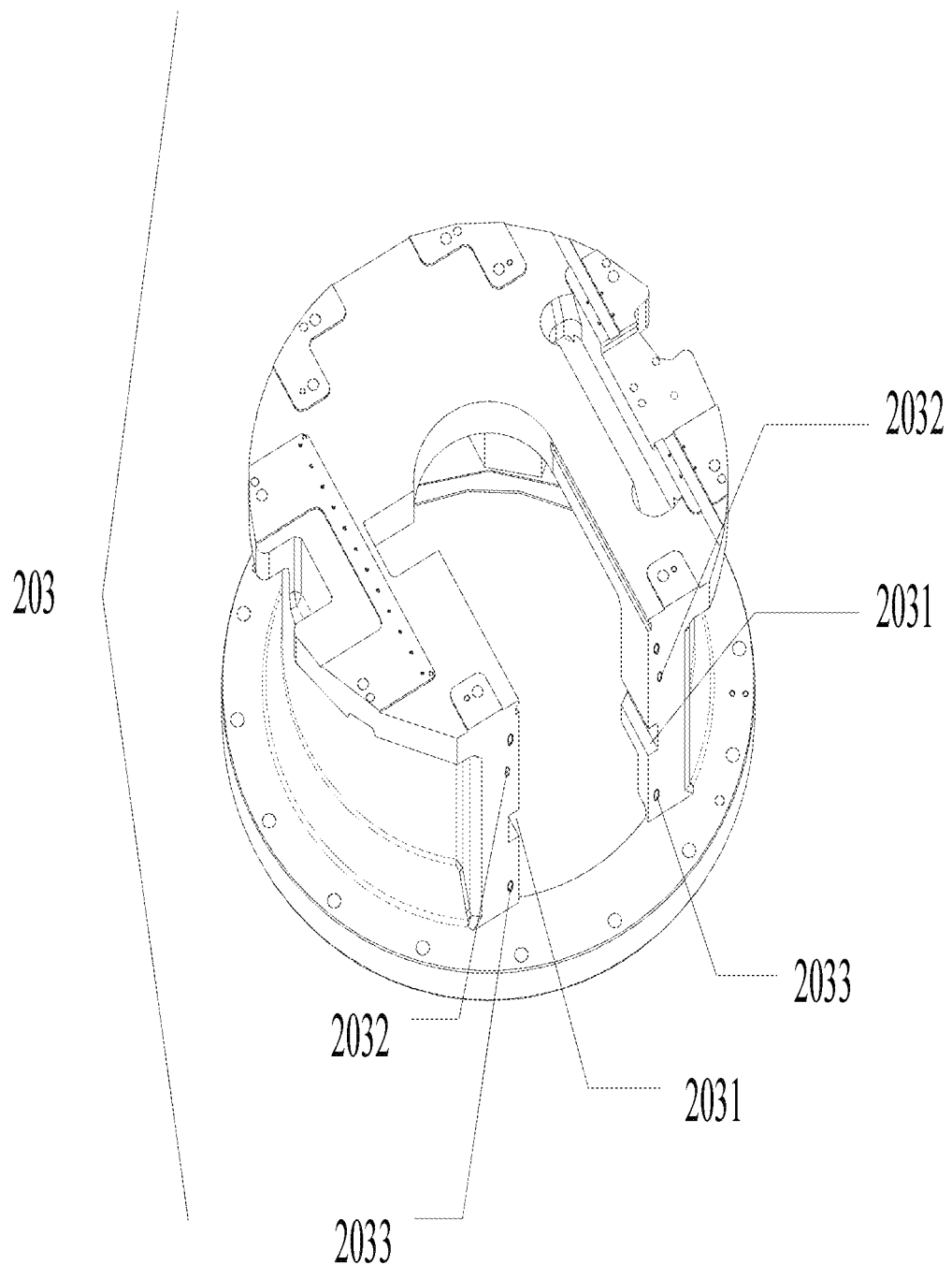
FIG. 12 is a schematic structural diagram of a mounting seat provided by an embodiment of the present disclosure.

For example, as shown in FIG. 12, FIG. 12 is a schematic structural diagram of a mounting seat of a beam shaping module of a medical accelerator provided by an embodiment of the present disclosure. The first sliding mechanism is a guide block (not shown in the figure), and the second sliding mechanism is a guide groove 2031, where the guide block may be formed on the surface of the jaw base (not shown in the figure) corresponding to the mounting seat 203. The guide groove 2031 may be formed on the mounting seat 203. Through the cooperation of the guide groove 2031 and the guide block, the jaw assembly may be slid to a preset position in the mounting seat 203, or the jaw assembly may be slid out of the mounting seat 203 and be separated from the mounting seat 203.

Specifically, referring to FIG. 12, the guide grooves 2031 are two, and are mounted on the left and right sides of the jaw base along a sliding direction of the jaw assembly, thereby providing more stable sliding status for the jaw base. The guide block is a structure adapted to a shape of the guide groove 2031, and a smoother sliding status is provided by the adaptation of the guide block and the guide groove 2013.

The guide groove 2031 of the embodiments of the present disclosure is not limited to two, and the mounting method is not limited to being mounted on the left and right sides of the jaw base, and other methods that can provide a stable sliding status for the jaw base may also be selected.

The guide block of the embodiments of the present disclosure is not limited to the state of shape adapting with the guide groove 2031. For example, in order to avoid collision between the guide block and the guide groove 2031, an inner surface of the guide groove has structures such as rounded corners.

Further, the connecting portion may include a first positioning mechanism mounted on the surface of the jaw base corresponding to the mounting seat, where the first positioning mechanism cooperates with a second positioning mechanism on the mounting seat such that positioning between the jaw assembly and the mounting seat is implemented through the first positioning mechanism and the second positioning mechanism.

For example, as shown in FIG. 12, the first positioning mechanism may be a positioning pin, and the second positioning mechanism may be a positioning pin hole 2032 on the mounting seat 203, and the positioning pin hole 2032 matches the positioning pin. When the positioning pins are respectively inserted into the matching positioning pin holes 2032, it may be ensured that a relative position between the jaw assembly and the mounting seat 203 is a preset relative position, that is, to achieve a positioning purpose between the jaw assembly and the mounting seat 203. Specifically, the positioning pins are a plurality of positioning pins respectively mounted on the left and right sides of the jaw base along the sliding direction of the jaw assembly. The positioning pin holes 2032 are respectively installed on the left and right sides of the mounting seat 203 along the sliding direction of the jaw assembly.

Further, the connecting portion may include a first stationary mechanism mounted on the surface of the jaw base corresponding to the mounting seat, the first stationary mechanism cooperates with a second stationary mechanism on the mounting seat, and the first fixing mechanism and the second stationary mechanism is fixed by a third stationary mechanism to implement fixing between the jaw assembly and the mounting seat.

For example, as shown in FIG. 12, a third positioning mechanism (not shown in the figure) may be a mounting bolt, the second stationary mechanism may be a mounting base threaded hole 2033, and the first stationary mechanism may be a jaw assembly threaded hole (not shown in the figure). The mounting seat 203 is formed with the mounting base threaded hole 2033 which is matched with the mounting bolt. The jaw assembly (not shown in the figure) is formed with the jaw assembly threaded hole which is matched with the mounting bolt. The mounting bolt is configured to pass through the mounting base threaded hole 2033 and the jaw assembly threaded hole to connect the mounting seat 203 with the jaw assembly.

Specifically, the jaw assembly threaded holes are multiple, and are respectively disposed on the left and right sides of the jaw base along the sliding direction of the jaw assembly. The mounting base threaded holes are multiple, and are respectively disposed on the left and right sides of the mounting seat along the sliding direction of the jaw assembly.

Therefore, in the embodiments of the present disclosure, a plurality of mounting bolts pass through a plurality of mounting base threaded holes 2033 and a plurality of jaw assembly threaded holes to connect the mounting seat 203 with the jaw assembly, which may fix the jaw assembly more firmly on the mounting seat 203, avoiding a relative movement between the jaw assembly and the mounting seat 203 to affect the normal operation of the medical accelerator.

Figure 2:
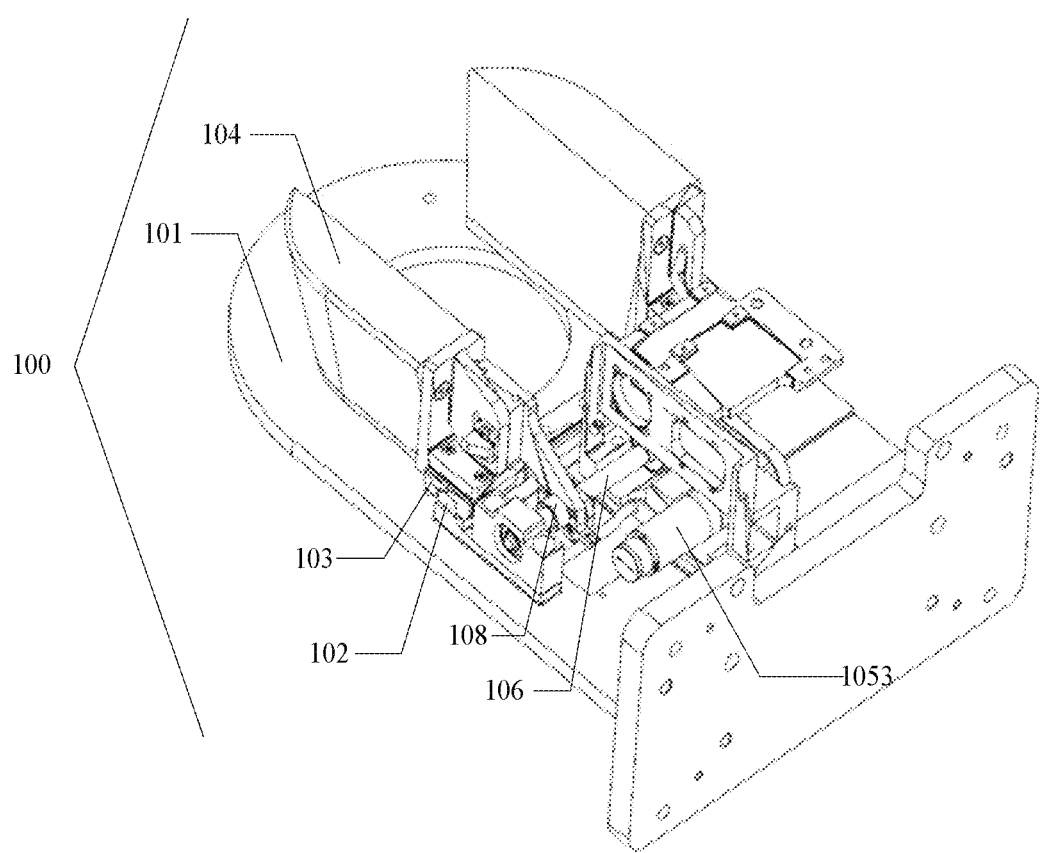
FIG. 2 is a schematic structural diagram of a jaw assembly provided by an embodiment of the present disclosure.

Alternatively, as shown in FIG. 1 and FIG. 2, FIG. 2 is a schematic structural diagram of a jaw assembly provided by an embodiment of the present disclosure. In an embodiment of the present disclosure, the moving assembly includes a sliding rail 102 and a slider 103 correspondingly connected to the jaw body 104, the sliding rail 102 is disposed on a surface of the jaw base 101 bearing the jaw body 104 along a moving in or out direction of the jaw body 104, and the jaw body 104 moves along the sliding rail 102 through the slider 103. By making the moving assembly be composed of the sliding rail 102 and the slider 103, and dispose the sliding rail 102 on the surface of the jaw base 101 bearing the jaw body 104 along the moving in or out direction of the jaw body 104, it may be ensured that the jaw body 104 can move along the surface of the jaw base 101 relatively stably.

The sliding rail may be a jaw shared sliding rail, and the jaw body moves along the jaw shared sliding rail through the slider.

Figure 3:
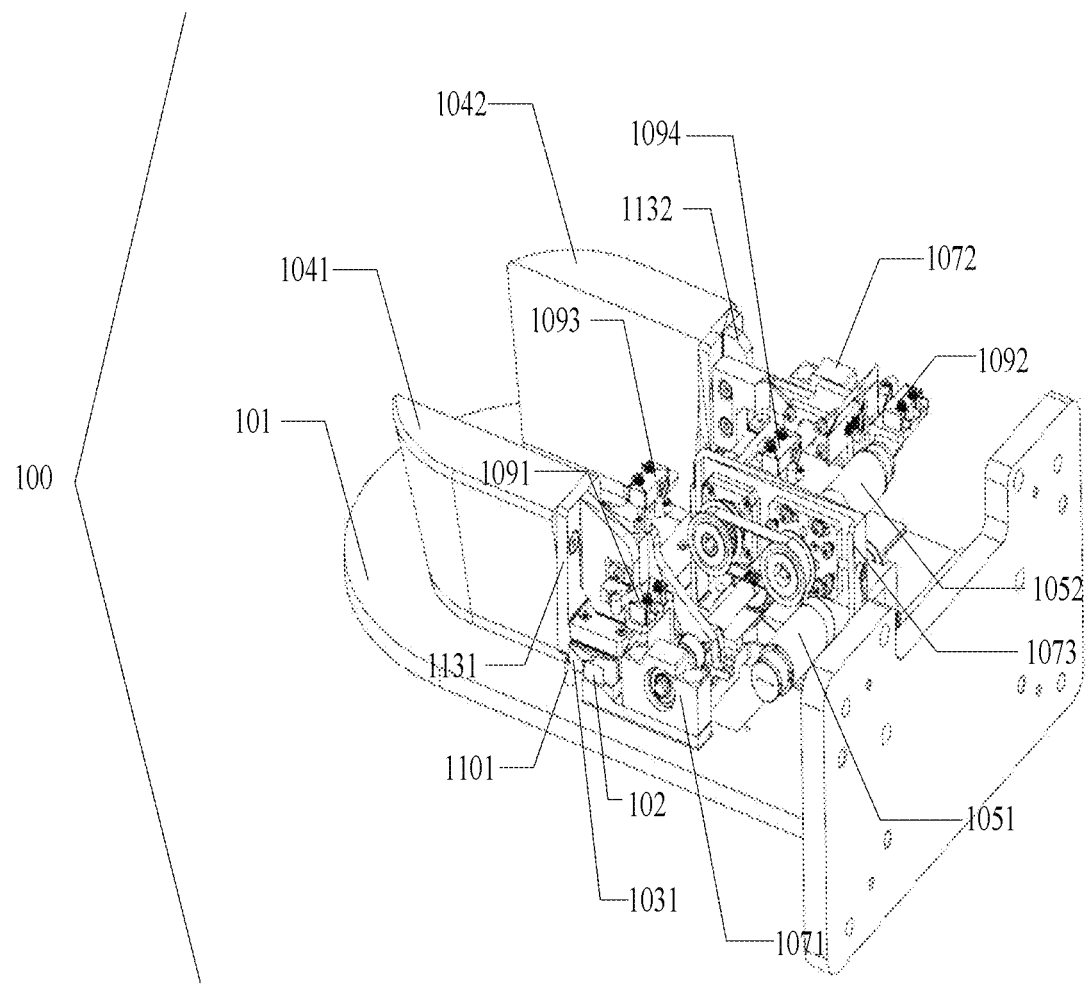
FIG. 3 is a schematic structural diagram of a jaw assembly provided by an embodiment of the present disclosure.
Figure 4:
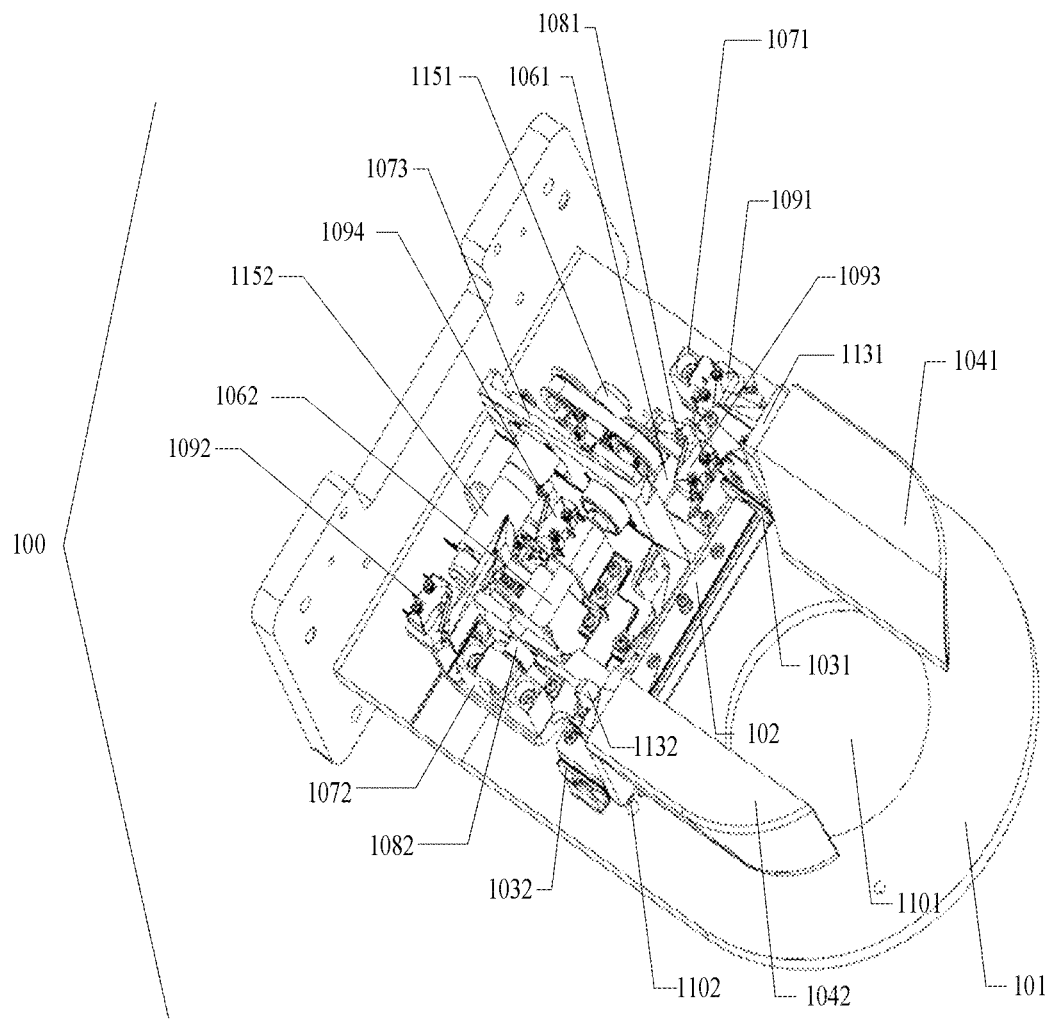
FIG. 4 is a schematic structural diagram of a jaw assembly provided by an embodiment of the present disclosure.

For example, as shown in FIG. 3 and FIG. 4, FIG. 3 is a schematic structural diagram of a jaw assembly provided by an embodiment of the present disclosure, and FIG. 4 is a schematic structural diagram of a jaw assembly provided by an embodiment of the present disclosure. The jaw assembly 100 includes a first jaw body 1041, a second jaw body 1042, the moving assembly includes a first slider 1031, a second slider 1032, and the sliding rail 102 (that is, the jaw shared sliding rail). The first jaw body 1041 is connected to the first slider 1031, the second jaw body 1042 is connected to the second slider 1032, the first slider 1031 and the second slider 1032 are both slidably connected to the sliding rail 102, so that the first jaw body 1041 and the second jaw body 1042 both move on the sliding rail 102 by the corresponding slider. Specifically, the sliding rail 102 may be disposed along a movement direction of the first jaw body 1041 or the second jaw body 1042. The embodiments of the present disclosure reduce the number of sliding rails disposed on the jaw base 101 under the premise of ensuring that a plurality of jaw bodies (for example, the first jaw body 1041 and the second jaw body 1042) can move normally, to prevent the jaw base 101 from occupying too much space due to an excessive number of parts and causing the volume to be too large.

It should be noted that in an embodiment, the jaw assembly may also have a plurality of sliding rails, but at least one of the sliding rails may be shared by a plurality of jaw bodies. For example, the jaw assembly may include N jaw bodies and N−1 sliding rails, and at least one of the sliding rails is shared by at least two jaw bodies.

Alternatively, as shown in FIG. 3 and FIG. 4, in an embodiment of the present disclosure, the jaw assembly 100 includes a first jaw body 1041, a second jaw body 1042, a first drive apparatus 1051, and a second drive apparatus 1052, the first jaw body 1041 is connected to the jaw base 101 through the moving assembly 130, the second jaw body 1042 is connected to the jaw base 101 through the moving assembly 130, the first drive apparatus 1051 is connected to the first jaw body 1041 and is configured to drive the first jaw body 1041 to move along the moving assembly 130, the second drive apparatus 1052 is connected to the second jaw body 1042 and is configured to drive the second jaw body 1042 to move along the moving assembly 130, and the first drive apparatus 1051 and the second drive apparatus 1052 are stacked along a beam transmission direction.

Due to large volume of the drive apparatus (for example, the first drive apparatus 1051 and the second drive apparatus 1052), by stacking the first drive apparatus 1051 and the second drive apparatus 1052 along the beam transmission direction, a space utilization rate in the jaw assembly may be improved, a total volume of the jaw assembly is reduced, and the jaw assembly is convenient for a user to store and set in the medical accelerator, thereby improving the user experience.

Alternatively, in an embodiment of the present disclosure, the jaw further includes at least one support, the at least one support is disposed on a surface of the jaw base bearing the jaw body, the first drive apparatus and the second drive apparatus are respectively connected to the at least one support, and are stacked along the beam transmission direction through the support. For example, as shown in FIG. 3 and FIG. 4, the jaw further includes an intermediate support 1073, the intermediate support 1073 is disposed on the surface of the jaw base 101 bearing the first jaw body 1041 and the second jaw body 1042, the first drive apparatus 1051 and the second drive apparatus 1052 are respectively connected to the intermediate support 1073, and are stacked along the beam transmission direction through the intermediate support 1073. The embodiment of the present disclosure realizes a stack arrangement of the first drive apparatus 1051 and the second drive apparatus 1052 through the intermediate support 1073, thereby improving the space utilization rate in the jaw assembly and reducing the volume of the jaw assembly.

Alternatively, in an embodiment of the present disclosure, the first drive apparatus and/or the second drive apparatus may include: a power apparatus, at least one lead screw and at least one lead screw nut, the lead screw nut is sleeved on the lead screw, the jaw body is connected to the lead screw nut, the lead screw is disposed along a moving in or out direction of the jaw body, and an output shaft of the power apparatus is in transmission connection with the lead screw for driving the lead screw to rotate, so that the lead screw nut drives the jaw body to move along the lead screw. For example, taking one of the first drive apparatus and the second drive apparatus as an example, as shown in FIG. 1 and FIG. 2, the first drive apparatus may include a lead screw 106, a power apparatus 1053 and a lead screw nut 108. The lead screw nut 108 is sleeved on the lead screw 106, the jaw body 104 is connected to the lead screw nut 108, the lead screw 106 is disposed along the moving in or out direction of the jaw body 104, and the output shaft of the power apparatus 1053 (not shown in the figure) is in transmission connection with the lead screw 106 for driving the lead screw 106 to rotate, so that the lead screw nut 108 drives the jaw body 104 to move along the lead screw 106.

The lead screw nut 108 may be directly connected to the jaw body 104, or the lead screw nut 108 may be connected to the jaw body through a connector (not shown in the figure), where the connector may also be configured to connect the jaw body 104 and the slider 103.

It should be noted that at least one of the first drive apparatus and the second drive apparatus may only include one power apparatus, one lead screw and one lead screw nut, and at least one of the first drive apparatus and the second drive apparatus may also include a plurality of power apparatuses, a plurality of lead screws and a plurality of lead screw nuts, which is not limited in the embodiments of the present disclosure.

By making the first drive apparatus and/or the second drive apparatus be composed of the power apparatus, at least one lead screw and at least one lead screw nut, sleeve the lead screw nut on the lead screw, connect the jaw body to the lead screw nut, dispose the lead screw along the moving in or out direction of the jaw body, transmission connect the output shaft of the power apparatus to the lead screw for driving the lead screw to rotate, so that the lead screw nut drives the jaw body to move along the lead screw to control rotation of a rotating shaft of the drive apparatus, to drive the lead screw to rotate, and the lead screw nut sleeved on the lead screw moves along the lead screw, since the lead screw is disposed along the moving in or out direction of the jaw body, the lead screw nut may drive the jaw body to move, simplifying steps of adjusting a position of the jaw body, facilitating user operations, and improving the user experience.

Alternatively, as shown in FIG. 3 and FIG. 4, in an embodiment of the present disclosure, the first drive apparatus includes a first power apparatus 1151, a first lead screw 1061 and a first lead screw nut 1081, and the second drive apparatus includes a second power apparatus 1152, a second lead screw 1062, and a second lead screw nut 1082. The jaw includes a first support 1071, a second support 1072, and an intermediate support 1073, the first support 1071, the second support 1072, and the intermediate support 1073 are all disposed on the surface of the jaw base 101 bearing the jaw body (for example, the first jaw body 1041 and the second jaw body 1042), and the first support 1071 and the second support 1072 are disposed oppositely, and the intermediate support 1073 is disposed between the first support 1071 and the second support 1072.

A first end of the first lead screw 1061 is rotatably connected to the first support 1071, a second end of the first lead screw 1061 is rotatably connected to the intermediate support 1073, a first end of the second lead screw 1062 is rotatably connected to the second support 1072, a second end of the second lead screw 1062 is rotatably connected to the intermediate support 1073, and a distance between the first lead screw 1061 and the jaw base 101 is greater than a distance between the second lead screw 1062 and the jaw base 101. The first power apparatus 1151 and the second power apparatus 1152 are both connected to the intermediate support 1073, and a distance between the first power apparatus 1151 and the jaw base 101 is greater than a distance between the second power apparatus 1152 and the jaw base 101, an output shaft of the first power apparatus 1151 is in transmission connection with the first lead screw 1061, and an output shaft of the second power apparatus 1152 is in transmission connection with the second lead screw 1062.

In addition, by equipping each jaw body in the jaw assembly with its own corresponding power apparatus, slider, lead screw, and lead screw nut, each jaw body may independently adjust its position, which reduces a chance of failure.

Alternatively, as shown in FIG. 3 and FIG. 4, in an embodiment of the present disclosure, the jaw assembly 100 may further include a first limit switch 1091 and a second limit switch 1092. The first limit switch 1091 is disposed on the surface of the jaw base 101 bearing the jaw body (such as the first jaw body 1041 or the second jaw body 1042), is configured to be triggered when a distance between the first jaw body 1041 and an end of the sliding rail 102 that extends along the moving in or out direction of the jaw body (for example, the first jaw body 1041 or the second jaw body 1042) is less than or equal to a first trigger distance threshold. The second limit switch 1092 is disposed on the surface of the jaw base 101 bearing the jaw body (such as the first jaw body 1041 or the second jaw body 1042), is configured to be triggered when a distance between the second jaw body 1042 and another end of the sliding rail 102 that extends along the moving in or out direction of the jaw body (such as the first jaw body 1041 or the second jaw body 1042) is less than or equal to a second trigger distance threshold. The first trigger distance threshold and the second trigger distance threshold are both set by those skilled in the art as needed.

The first limit switch may be triggered by the first jaw body 1041, or by the first slider 1031 or a connector 1131 between the first jaw body 1041 and the first slider 1031, which is not limited in the present disclosure. The first limit switch 1091 may send a first triggered signal when it is triggered, so that the user can determine based on the first triggered signal that the distance between the first jaw body 1041 and the end of the sliding rail 102 along the moving in or out direction of the jaw body (for example, the first jaw body 1041 or the second jaw body 1042) is too close, and the first jaw body 1041 should stop sliding along the sliding rail 102 to prevent the first jaw body 1041 from sliding beyond an allowable scope of movement and colliding with other parts and causing damage. The second limit switch 1092 may be triggered by the second jaw body 1042, or by the second slider 1032 or a connector 1132 between the second jaw body 1042 and the second slider 1032, which is not limited in the present disclosure. The second limit switch 1092 may send a second triggered signal when it is triggered, so that the user can determine based on the second triggered signal that the distance between the second jaw body 1042 and the other end of the sliding rail 102 along the moving in or out direction of the jaw body (for example, the first jaw body 1041 or the second jaw body 1042) is too close, and the second jaw body 1042 should stop sliding along the sliding rail to prevent the second jaw body 1042 from sliding beyond an allowable scope of movement and colliding with other parts and causing damage. Alternatively, as shown in FIG. 3 and FIG. 4, in an embodiment of the present disclosure, the jaw assembly 100 may further include a third limit switch 1093 and a fourth limit switch 1094. The third limit switch 1093 is connected to the first lead screw nut 1081, and is configured to be triggered when a distance between the first lead screw nut 1081 and the intermediate support 1073 is less than or equal to a third trigger distance threshold. The fourth limit switch 1094 is connected to the intermediate support 1073, and is configured to be triggered when a distance between the second lead screw nut 1082 and the intermediate support 1073 is less than or equal to a fourth trigger distance threshold. The third trigger distance threshold and the fourth trigger distance threshold are both set by those skilled in the art as needed.

The third limit switch 1093 may be triggered by the intermediate support 1073, or by other components (not shown in the figure) connected to the intermediate support 1073, which is not limited in the present disclosure. The third limit switch 1093 may send a third triggered signal when it is triggered, so that the user can determine based on the third triggered signal that a distance between the intermediate support 1073 and the first lead screw nut 1081 is too close, and the first lead screw nut 1081 should stop sliding towards the intermediate support 1073 to avoid collision between the first jaw body 1041 and the second jaw body 1042. The fourth limit switch 1094 may be triggered by the second lead screw nut 1082, or by other components (not shown in the figure) connected to the second lead screw nut 1082, which is not limited in the present disclosure. The fourth limit switch 1094 may send a fourth triggered signal when it is triggered, so that the user can determine based on the fourth triggered signal that a distance between the intermediate support 1073 and the second lead screw nut 1082 is too close, and the second lead screw nut 1082 should stop sliding towards the intermediate support 1073 to avoid collision between the first jaw body 1041 and the second jaw body 1042.

Alternatively, as shown in FIG. 3 and FIG. 4, in an embodiment of the present disclosure, the jaw assembly may further include a first limit portion 1101 and a second limit portion 1102. The first limit portion 1101 is disposed on a first surface of the jaw base 101 and is configured to attach to the first slider 1031 when the distance between the first jaw body 1041 and the end of the sliding rail 102 that extends along the moving in or out direction of the jaw body (for example, the first jaw body 1041 or the second jaw body 1042) is less than or equal to a first limit distance threshold. The second limit portion 1102 is disposed on the first surface of the jaw base 101 and is configured to attach to the second slider 1032 when the distance between the second jaw body 1042 and the other end of the sliding rail 102 that extends along the moving in or out direction of the jaw body (for example, the first jaw body 1041 or the second jaw body 1042) is less than or equal to a second limit distance threshold. The first limit distance threshold and the second limit distance threshold are both set by those skilled in the art as needed.

By making the first limit portion 1101 attach to the first slider 1031 when the distance between the first jaw body 1041 and the end of the sliding rail 102 that extends along the moving in or out direction of the jaw body (for example, the first jaw body 1041 or the second jaw body 1042) is less than or equal to the first limit distance threshold, the first jaw body 1041 may be prevented from continuing sliding along the sliding rail 102, reducing a probability of the first jaw body 1041 colliding with other components due to sliding beyond the allowable scope of movement, thereby reducing a failure rate of the jaw assembly. At the same time, by making the second limit portion 1102 attach to the second slider 1032 when the distance between the second jaw body 1042 and the other end of the sliding rail 102 that extends along the moving in or out direction of the jaw body (for example, the first jaw body 1041 or the second jaw body 1042) is less than or equal to the second limit distance threshold, the second jaw body 1042 may be prevented from continuing sliding along the sliding rail 102, reducing a probability of the second jaw colliding with other components due to sliding beyond the allowable scope of movement, thereby reducing the failure rate of the jaw assembly.

Alternatively, as shown in FIG. 3 and FIG. 4, in an embodiment of the present disclosure, the jaw assembly may further include a third limit portion 1103 and a fourth limit portion 1104. The third limit portion 1103 is disposed on the first surface of the jaw base 101 and is configured to attach to the first slider 1031 when a distance between the first jaw body 1041 and the intermediate support 1073 is less than or equal to a third limit distance threshold. The fourth limit portion 1104 is disposed on the first surface of the jaw base 101 and is configured to attach to the second slider 1032 when a distance between the second jaw body 1042 and the intermediate support 1073 is less than or equal to a fourth limit distance threshold. The third limit distance threshold and the fourth limit distance threshold are both set by those skilled in the art as needed.

By making the third limit portion 1103 attach to the first slider 1031 when the distance between the first jaw body 1041 and the intermediate support 1073 is less than or equal to the third limit distance threshold, the first jaw body 1041 may be prevented from continuing sliding towards the intermediate support 1073, reducing a probability of damage to the first jaw body 1041 or the second jaw body 1042 due to collision of the first jaw body 1041 with the second jaw body 1042 that is also close to the intermediate support 1073, thereby reducing the failure rate of the jaw assembly. At the same time, by making the fourth limit portion 1104 attach to the second slider 1032 when the distance between the second jaw body 1042 and the intermediate support 1073 is less than or equal to the fourth limit distance threshold, the second jaw body 1042 may be prevented from continuing sliding towards the intermediate support 1073, reducing a probability of damage to the first jaw body 1041 or the second jaw body 1042 due to collision of the second jaw body 1042 with the first jaw body 1041 that is also close to the intermediate support 1073, thereby reducing the failure rate of the jaw assembly.

Figure 5:
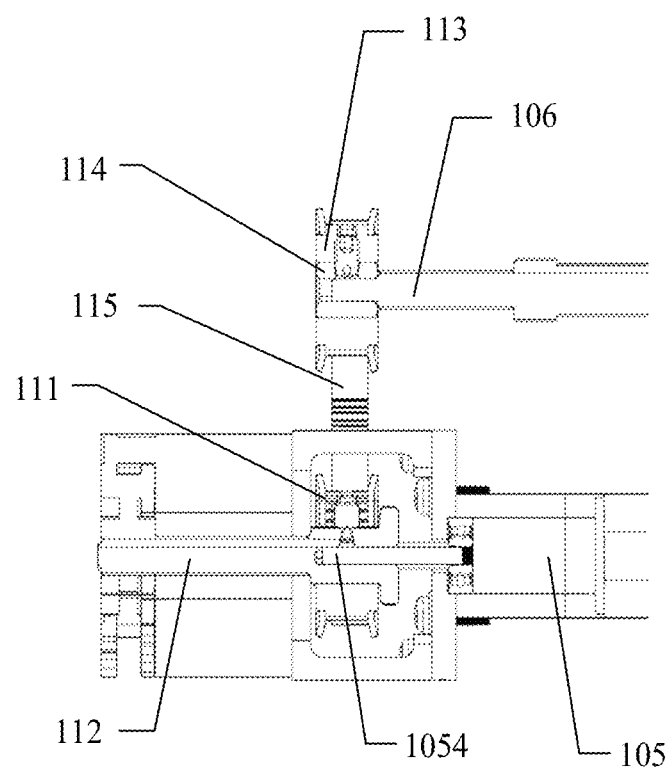
FIG. 5 is a schematic lateral cross-sectional view of a jaw assembly provided by an embodiment of the present disclosure.

Alternatively, the jaw assembly further includes a drive pulley, a drive adapter shaft, a lead screw pulley, and a lead screw adapter shaft; and the drive adapter shaft is connected to the output shaft of the power apparatus, the drive pulley is connected to the drive adapter shaft, the drive pulley is in transmission connection with the lead screw pulley through a synchronous belt, the lead screw pulley is connected to the lead screw adapter shaft, and the lead screw adapter shaft is connected to the lead screw. For example, as shown in FIG. 5, FIG. 5 is a schematic lateral cross-sectional view of a jaw assembly provided by an embodiment of the present disclosure. The jaw assembly further includes a drive pulley 111, a drive adapter shaft 112, a lead screw pulley 113, and a lead screw adapter shaft 114. The drive adapter shaft 112 is connected to the output shaft 1054 of the power apparatus 105, the drive pulley 111 is connected to the drive adapter shaft 112, the drive pulley 111 is in transmission connection with the lead screw pulley 113 through a synchronous belt 115, the lead screw pulley 113 is connected to the lead screw adapter shaft 114, and the lead screw adapter shaft 114 is connected to the lead screw 106.

Alternatively, a synchronous belt shield plate (not shown in the figure) may be disposed above the synchronous belt 115, and the synchronous belt shield plate may be disposed between the synchronous belt and the treatment head beam shaping module (not shown in the figure). The synchronous belt shield plate may be made of metal or other materials capable of shielding radiation rays, which is not specifically limited in the embodiments of the present disclosure. The synchronous belt shield plate shields radiation rays emitted by the treatment head beam shaping module to prevent the radiation rays from directly irradiating the synchronous belt 115 to extend the life of the synchronous belt 115.

In the solution provided by the embodiments of the present disclosure, when the lead screw 106 needs to be rotated, torque may be output through the output shaft 1054 of the power apparatus 105, and the drive adapter shaft 112 connected to the output shaft 1054 transmits the torque to the lead screw pulley 113 through the drive pulley 111 and the synchronous belt 115, so that the lead screw pulley 113 drives the lead screw adapter shaft 114 and the lead screw 106 connected to the lead screw adapter shaft 114 to rotate.

In the embodiment of the present disclosure, the drive pulley 111, the synchronous belt 115, and the lead screw pulley 113 drive the lead screw adapter shaft 114 and the lead screw 106 connected to the lead screw adapter shaft 114 to rotate, so that the power apparatus 105 and the lead screw 106 of the jaw assembly may be disposed side by side in the jaw assembly, reducing the volume of the jaw assembly. At the same time, since it is convenient to replace the synchronous belt 115 that is prone to wear, the embodiment of the present disclosure simplifies the maintenance difficulty of the jaw assembly.

Figure 6:
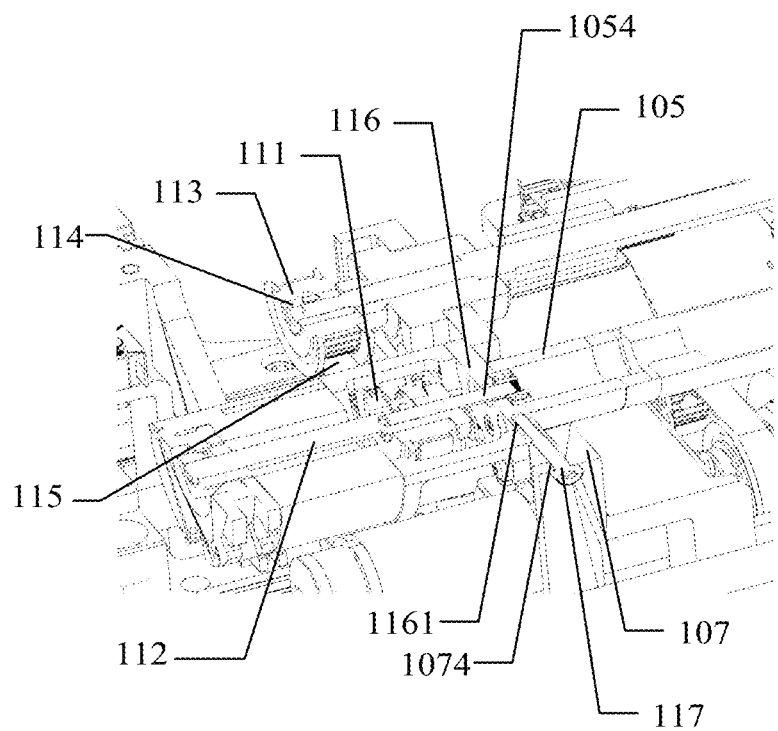
FIG. 6 is a schematic structural diagram of a jaw assembly provided by an embodiment of the present disclosure.

Alternatively, as shown in FIG. 6, FIG. 6 is a schematic structural diagram of a jaw assembly provided by an embodiment of the present disclosure. In an embodiment of the present disclosure, the jaw assembly also includes a power apparatus flange 116 and a pulley adjustment screw 117. The power apparatus 105 is connected to the power apparatus flange 116. A side wall of the power apparatus flange 116 forms a waist-shaped hole 1161 matching the pulley adjustment screw 117. A support 107 forms a opening 1074 matching the pulley adjustment screw 117. The pulley adjustment screw 117 passes through the opening 1074, so that a head of the pulley adjustment screw 117 fits the support 107, and the pulley adjustment screw 117 is screwed into the waist-shaped hole 1161 to fix the power apparatus flange 116 on the support 107.

The pulley adjustment screw 117 is also configured to rotate the power apparatus flange 116 in a first clock direction to move in a first adjustment direction, or rotate in a second clock direction to move the power apparatus flange 116 in a second adjustment direction. The first adjustment direction and the second adjustment direction are both parallel to an axial direction of the pulley adjustment screw 117, and the first adjustment direction is opposite to the second adjustment direction. Specifically, the first clock direction may be clockwise, and the second clock direction may be counterclockwise; or the first clock direction may be counterclockwise, and the second clock direction may be clockwise. In actual use, those skilled in the art may set the first clock direction and the second clock direction as needed.

A position of the power apparatus flange 116 may be adjusted by rotating the pulley adjustment screw 117. Since the power apparatus 105 is connected to the power apparatus flange 116, and the output shaft 1054 of the power apparatus 105 is connected to the drive pulley 111 through the drive adapter shaft 112, a position of the drive pulley 111 may be adjusted by rotating the pulley adjustment screw 117, and then a shaft center distance between the drive pulley 111 and the lead screw pulley 113 may be adjusted, to achieve the purpose of tensioning or loosening the synchronous belt 115 transmission connecting the drive pulley 111 and the lead screw pulley 113, which reduces the difficulty of tensioning or loosening the synchronous belt 115, and improves the user experience.

Figure 7:
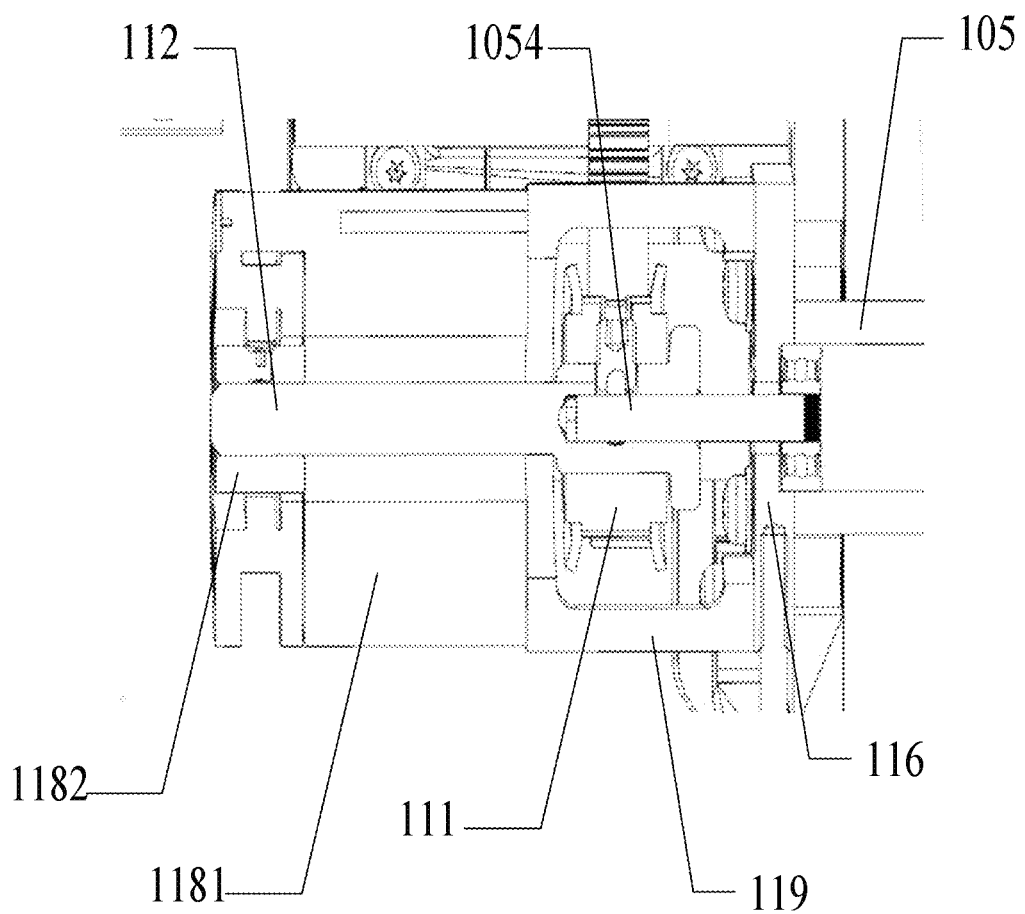
FIG. 7 is a schematic lateral cross-sectional view of a jaw assembly provided by an embodiment of the present disclosure.

Alternatively, as shown in FIG. 7, FIG. 7 is a schematic lateral cross-sectional view of a jaw assembly provided by an embodiment of the present disclosure. In an embodiment of the present disclosure, the jaw assembly further includes a band-type brake apparatus and a band-type brake bracket 119. The band-type brake apparatus includes a band-type brake fixing portion 1181 and a band-type brake movable portion 1182 that are rotatably connected. The band-type brake fixing portion 118 is connected to the power apparatus flange 116 through the band-type brake bracket 119, and the band-type brake movable portion 1182 is connected to the drive adapter shaft 112.

The band-type brake apparatus is configured to make the band-type brake movable portion 1182 and the band-type brake fixing portion 1181 hold tightly in response to a holding control signal; or the band-type brake apparatus is configured to loose the band-type brake movable portion 1182 and the band-type brake fixing portion 1181 in response to a loose control signal. Or, the band-type brake apparatus is configured to make the band-type brake movable portion 1182 and the band-type brake fixing portion 1181 hold tightly in response to a holding control signal, and is also configured to loose the band-type brake movable portion 1182 and the band-type brake fixing portion 1181 in response to a loose control signal.

By holding the band-type brake movable portion 1182 and the band-type brake fixing portion 1181 tightly, the drive adapter shaft 112 may not be rotated, so that the output shaft 1054 of the power apparatus 105 connected to the drive adapter shaft 112 cannot output torque to the lead screw (not shown in the figure), it may ensure that the jaw body (not shown in the figure) cannot be driven by the lead screw, avoiding malfunction of the jaw body due to random movement and collision, and reducing a chance of failure of the jaw. By loosing the band-type brake movable portion 1182 and the band-type brake fixing portion 1181, it may ensure that the drive adapter shaft 112 can rotate normally, so that the output shaft 1054 of the power apparatus 105 connected to the drive adapter shaft 112 can output torque to the lead screw (not shown in the figure), ensuring that the jaw body can be normally driven by the lead screw, and the jaw assembly can move normally.

Figure 8:
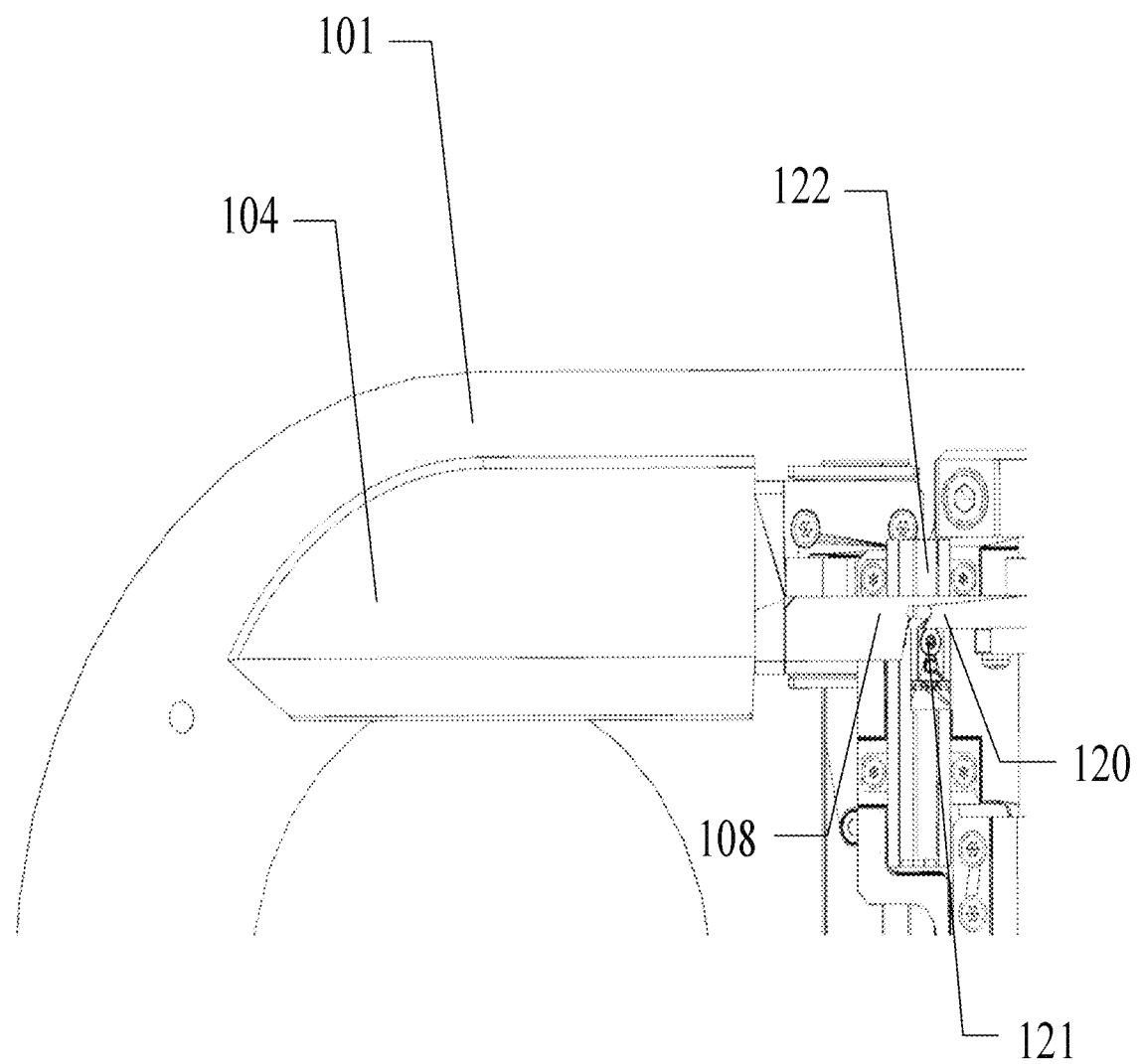
FIG. 8 is a schematic structural diagram of a jaw assembly provided by an embodiment of the present disclosure.

Alternatively, as shown in FIG. 8, FIG. 8 is a schematic structural diagram of a jaw assembly provided by an embodiment of the present disclosure. In an embodiment of the present disclosure, the jaw assembly further includes a shift fork 120, a resistance bar slider 121 and a resistance bar 122, one end of the shift fork 120 is connected to the resistance bar slider 121, the other end of the shift fork 120 is connected to the lead screw nut 108, the resistance bar 122 is disposed on the first surface of the jaw base 101, and the resistance bar slider 121 is configured to slide along the resistance bar 122 under drive of the lead screw nut 108. In the solution provided by the embodiments of the present disclosure, since the resistance bar slider 121 may slide along the resistance bar 122 under the drive of the lead screw nut 108 and the shift fork 120, a resistance passing through the resistance bar slider 121 and the resistance bar 122 changes. By detecting the resistance, a real-time position of the lead screw nut 108 may be determined based on a resistance detection result, so as to further estimate a real-time position of the jaw body 104 based on the real-time position of the lead screw nut 108, so that the user can control the jaw assembly based on the real-time position of the jaw body 104, which improves the user experience.

Specifically, in order to replace the resistance bar 121, the jaw assembly may further include an adapter plate (not shown in the figure), the jaw base 101 may form an adapter opening (not shown in the figure) for accommodating the adapter plate, and the resistance bar 122 is connected to the jaw base 101 through the adapter plate. When replacing the resistance bar 122, the adapter plate and the resistance bar 122 may be removed together, and then the resistance bar 122 may be replaced. After the replacement, the adapter plate and the resistance bar 122 may be placed together in the adapter through hole for installation. It is easier and more convenient to remove the adapter plate and the resistance bar 122 together than removing the resistance bar 122 separately. Therefore, the above solution reduces the difficulty of replacing the resistance bar 122 and reduces the maintenance difficulty of the jaw assembly.

Figure 9:
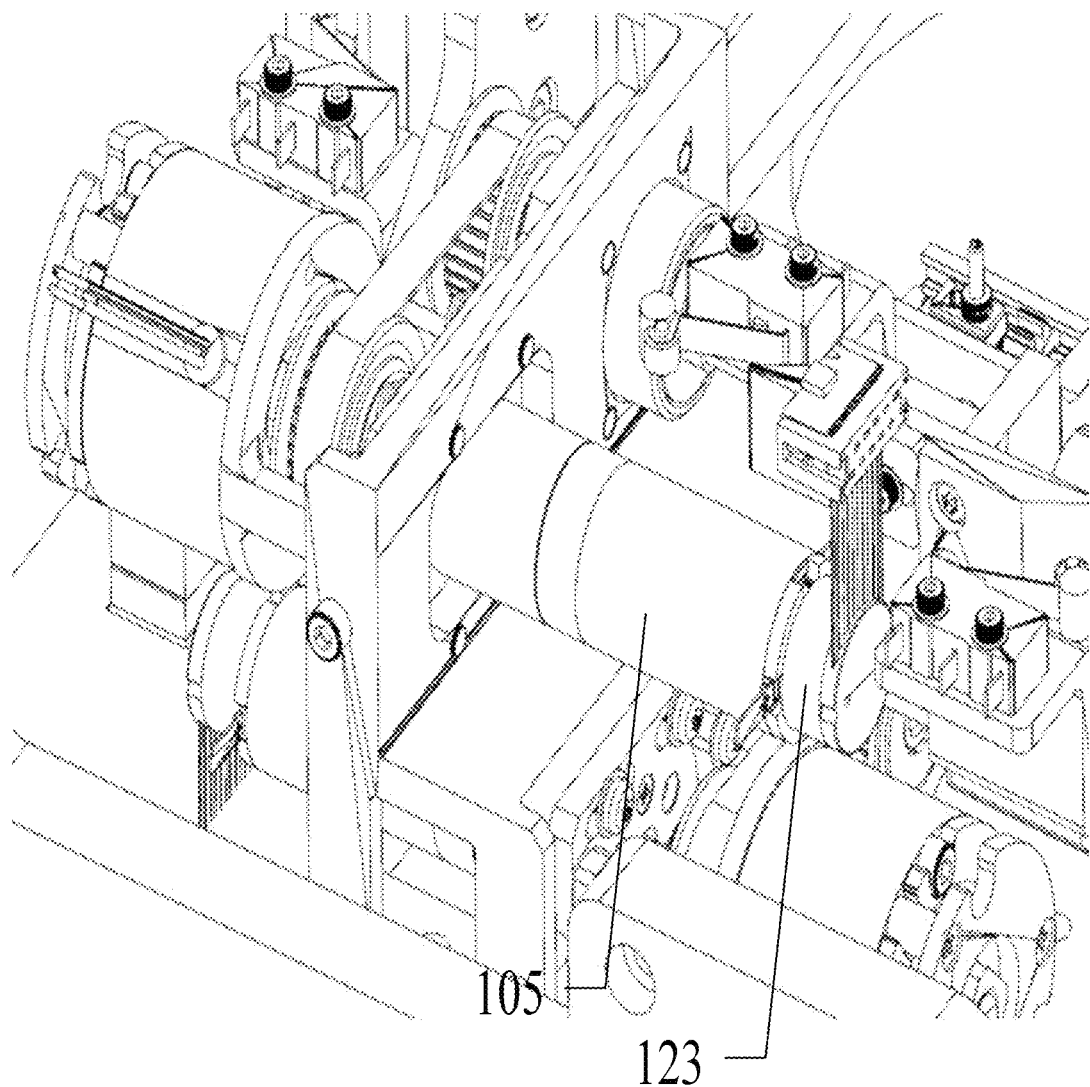
FIG. 9 is a schematic structural diagram of a jaw assembly provided by an embodiment of the present disclosure.

Alternatively, as shown in FIG. 9, FIG. 9 is a schematic structural diagram of a jaw assembly provided by an embodiment of the present disclosure. In an embodiment of the present disclosure, the jaw assembly further includes an encoder 123. The encoder 123 is connected to the output shaft (not shown in the figure) of the power apparatus 105, and the encoder 123 is configured to rotate under the drive of the output shaft of the power apparatus 105, so as to realize a detection function of the output shaft. Through a detection result, a real-time number of rotations of the output shaft of the power apparatus 105 may be obtained, so that a theoretical movement distance of the lead screw nut connected to the power output shaft can be obtained based on the real-time number of rotations. The theoretical movement distance is compared with an actual movement distance of the lead screw nut detected by the resistance bar and the resistance bar slider, so as to feed back whether a transmission apparatus fails and ensure an effective output of the power apparatus.

Figure 10:
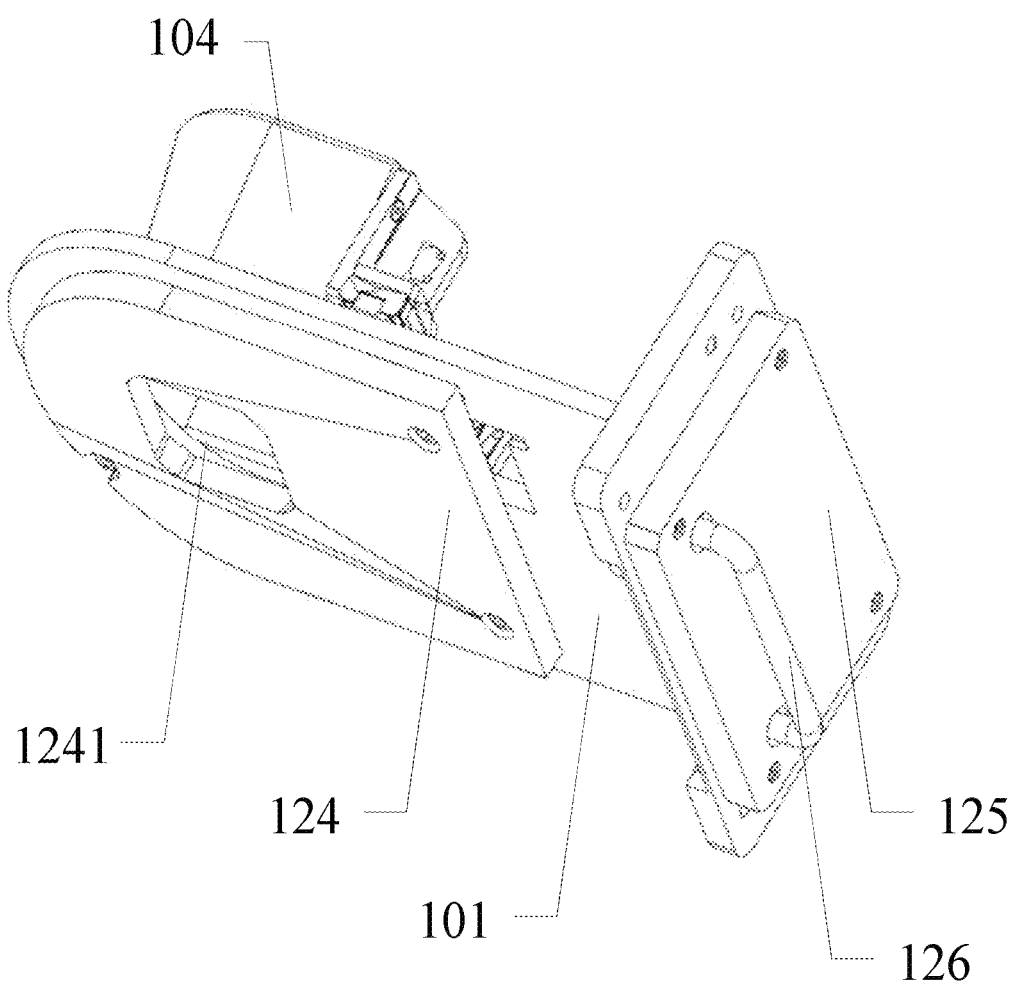
FIG. 10 is a schematic structural diagram of a jaw assembly provided by an embodiment of the present disclosure.

Alternatively, as shown in FIG. 10, FIG. 10 is a schematic structural diagram of a jaw assembly provided by an embodiment of the present disclosure. In an embodiment of the present disclosure, the jaw assembly 100 further includes a first shield block 124 disposed on a surface of the jaw base 101 opposite to the mounting seat (not shown in the figure), the first shield block 124 includes a shield block through hole 1241, and a position of the shield block through hole 1241 corresponds to a position of the beam opening (not shown in the figure). The first shield block 124 may be made of metal or other materials capable of shielding radiation rays, which is not specifically limited in the embodiments of the present disclosure. The first shield block 124 may prevent radiation rays emitted by the treatment head beam shaping module from transmitting through other parts of the jaw base 101 except the beam opening, resulting in radiation leakage.

Alternatively, as shown in FIG. 10, in an embodiment of the present disclosure, the jaw assembly further includes a second shield block 125, the second shield block 125 is connected to the jaw base 101 and the second shield block 125 is perpendicular to the surface of the jaw base 101 bearing the jaw body 104. The second shield block 125 is configured to close an insertion port (not shown in the figure) for inserting the jaw assembly on the mounting seat (not shown in the figure), to shield radiation at an entrance of the mounting seat of the treatment head beam shaping module of the medical accelerator, preventing radiation rays from leaking through the insertion port.

Alternatively, as shown in FIG. 10, in an embodiment of the present disclosure, the jaw assembly further includes a push-pull operation portion 126 that performs push and pull operations, connected to the jaw base 101 and perpendicular to the surface of the jaw base 101 bearing the jaw body 104. Alternatively, the push-pull operation portion 126 may be made of a shielding material. By providing the push-pull operation portion 126, it is convenient for the user to push or pull the jaw base 101 using the push-pull operation portion 126 without affecting a shielding effect.

Figure 11:
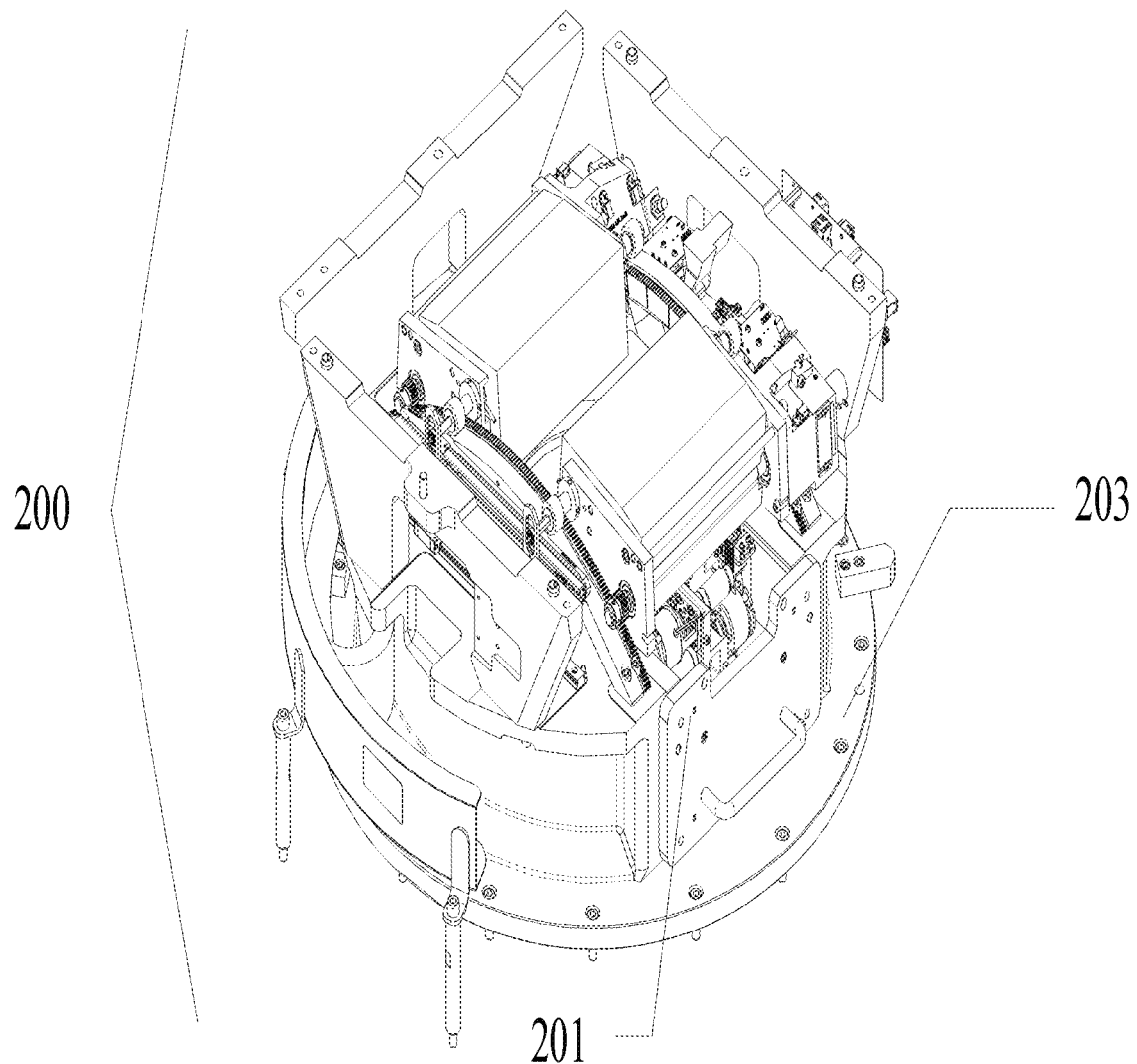
FIG. 11 is a schematic structural diagram of a medical accelerator provided by an embodiment of the present disclosure.

An embodiment of the present disclosure provides a medical accelerator, as shown in FIG. 11, FIG. 11 is a schematic structural diagram of a medical accelerator provided by an embodiment of the present disclosure. The medical accelerator 200 includes a mounting seat 203 and the jaw assembly 201 of any one of the above embodiments, and the mounting seat 203 is configured to mount a beam shaping module.

In an embodiment of the present disclosure, the provided medical accelerator includes the mounting seat and the jaw assembly, where the mounting seat is configured to mount the beam shaping module, and the jaw assembly includes a jaw base, a moving assembly and at least one set of jaws, each set of jaws including at least two jaw bodies. The jaw base is detachably connected to a mounting seat of a treatment head beam shaping module of a medical accelerator, and when the jaw base is mounted on the mounting seat, a beam opening formed is located under the treatment head beam shaping module. The jaw body is connected to the jaw base through the moving assembly, and the moving assembly is configured to move the jaw body to between the beam opening and the treatment head beam shaping module, or to move the jaw body out between the beam opening and the treatment head beam shaping module to adjust a beam flow through the beam opening. In the above solution, by removing the jaw base from the mounting seat of the treatment head beam shaping module of the medical accelerator, the jaw in the jaw assembly may be conveniently maintained. Therefore, the solution reduces the maintenance difficulty of the medical accelerator, and improves the user experience.

Alternatively, in an embodiment of the present disclosure, a second sliding mechanism may be formed on the mounting seat, and the second sliding mechanism may cooperate with a first sliding mechanism formed on the jaw assembly to implement separation and mounting between the jaw assembly and the mounting seat. For example, the second sliding mechanism may be a guide groove, and the first sliding mechanism may be a guide block. As shown in FIG. 12, FIG. 12 is a schematic structural diagram of a mounting seat provided by an embodiment of the present disclosure. The second sliding mechanism is a guide groove 2031, the first sliding mechanism is a guide block (not shown in the figure), the guide groove 2031 is formed on the mounting seat 203, and the guide block matched with the guide groove 2031 is formed on the jaw assembly (not shown in the figure). By forming the guide groove 2031 on the mounting seat 203 and forming the guide block matching the guide groove 2031 on the jaw assembly, it is convenient to insert the jaw assembly into the mounting seat along the guide groove.

Specifically, referring to FIG. 12, the guide grooves 2031 may be two, and the two guide grooves 2031 are mounted on the left and right sides of the jaw base along a sliding direction of the jaw assembly (not shown in the figure), thereby providing more stable sliding status for the jaw base. The guide block is a structure adapted to a shape of the guide groove 2031, and a smoother sliding status is provided by the adaptation of the guide block and the guide groove 2013.

The guide groove 2031 of the embodiments of the present disclosure is not limited to two, and the mounting method is not limited to being mounted on the left and right sides of the jaw base, and other methods that can provide a stable sliding status for the jaw base may also be selected.

The guide block of the embodiments of the present disclosure is not limited to the state of shape adapting with the guide groove 2031. For example, in order to avoid collision between the guide block and the guide groove, an inner surface of the guide groove has structures such as rounded corners.

Alternatively, the second positioning mechanism may be formed on the mounting seat, and the second positioning mechanism may cooperate with a first positioning mechanism formed on the jaw assembly to implement positioning between the jaw assembly and the mounting seat. For example, as shown in FIG. 12, in an embodiment of the present disclosure, the second positioning mechanism is a positioning pin hole 2032, the first positioning mechanism is a positioning pin (not shown in the figure), the positioning pin hole 2032 is formed on the mounting seat 203, and the positioning pin cooperating with the positioning pin hole 2032 is formed on the jaw assembly (not shown in the figure).

Specifically, the positioning pins are a plurality of positioning pins respectively mounted on the left and right sides of the jaw base along the sliding direction of the jaw assembly. The positioning pin holes 2032 are a plurality of positioning pin holes respectively disposed on the left and right sides of the mounting seat 203 along the sliding direction of the jaw assembly. Therefore, in the embodiments of the present disclosure, a plurality of positioning pins and a plurality of positioning pin holes cooperate to realize a more stable positioning between the jaw assembly and the mounting seat.

By forming the positioning pin hole 2032 on the mounting seat 203, and forming the positioning pin that cooperates with the positioning pin hole 2032 on the jaw assembly, it is possible for the user to position the jaw assembly at an accurate position more conveniently after inserting the jaw assembly into the mounting seat 203, thereby reducing the difficulty of positioning.

Alternatively, a second stationary mechanism may be formed on the mounting seat, and a third positioning mechanism may cooperate with a first stationary mechanism formed on the jaw assembly through the second stationary mechanism to implement fixing between the jaw assembly and the mounting seat. For example, as shown in FIG. 12, in an embodiment of the present disclosure, the medical accelerator further includes a mounting bolt (not shown in the figure), the second stationary mechanism may be a mounting base threaded hole 2033, the third positioning mechanism may be a mounting bolt, and the first stationary mechanism may be a jaw assembly threaded hole (not shown in the figure). The mounting seat 203 is formed with the mounting base threaded hole 2033 which is matched with the mounting bolt. The jaw assembly (not shown in the figure) is formed with the jaw assembly threaded hole which is matched with the mounting bolt. The mounting bolt is configured to pass through the mounting base threaded hole 2033 and the jaw assembly threaded hole to connect the mounting seat 203 with the jaw assembly. Specifically, the first stationary mechanisms are a plurality of stationary mechanism respectively mounted on the left and right sides of the jaw base along the sliding direction of the jaw assembly. The second stationary mechanisms are respectively mounted on the left and right sides of the mounting seat along the sliding direction of the jaw assembly.

By connecting the mounting seat 203 to the jaw assembly by passing the mounting bolt through the mounting base threaded hole 2033 and the jaw assembly threaded hole, the jaw assembly may be fixed firmly on the mounting seat 203, avoiding a relative movement between the jaw assembly and the mounting seat 203 to affect the normal operation of the medical accelerator.

It should be noted that the terms "including," "comprising," or any other variation thereof are intended to encompass non-exclusive inclusion, such that a process, method, product, or device that includes a series of elements includes not only those elements but also other elements not explicitly listed, or those that are inherent to such process, method, product, or device. Without more restrictions, elements defined by the sentence "including a . . . " do not exclude the existence of other identical elements in the process, method, product or device including the said elements.

The embodiments in this specification are described in a progressive method, and the same or similar parts between the embodiments may refer to each other. Each embodiment focuses on the differences from other embodiments. Specifically, for the system embodiment, since it is basically similar to the method embodiment, the description thereof is relatively simple. For related details, reference may be made to the part of description in the method embodiment.

The above description is merely embodiments of the present disclosure and is not intended to limit the present disclosure. For those skilled in the art, the present disclosure may have various modifications and changes. Any modification, equivalent replacement, improvement, etc. made within the spirit and principle of the present disclosure shall be included in the scope of the claims of the present disclosure.

What is claimed is:

1. A jaw assembly, comprising: a jaw base, a moving assembly and at least one set of jaws, each set of jaws comprising at least two jaw bodies;
    the jaw base is configured to be detachably connected to a mounting seat of a treatment head beam shaping module of a medical accelerator, and, when the jaw base is mounted on the mounting seat, a beam opening formed is located under the treatment head beam shaping module; and
    the jaw body is connected to the jaw base through the moving assembly, and the moving assembly is configured to move the jaw body to between the beam opening and the treatment head beam shaping module, or to move the jaw body out between the beam opening and the treatment head beam shaping module to adjust a beam flow through the beam opening,
    wherein the jaw base further comprises a connecting portion configured to be detachably connected to the mounting seat of the treatment head beam shaping module, the connecting portion comprises a first sliding mechanism mounted on a surface of the jaw base corresponding to the mounting seat of the treatment head beam shaping module, the first sliding mechanism is adapted to be slidable relative to a second sliding mechanism on the mounting seat of the treatment head beam shaping module such that the jaw assembly is slidable into and out of the mounting seat of the treatment head beam shaping module.

2. The jaw assembly according to claim 1, wherein the connecting portion comprises: a first positioning mechanism mounted on the surface of the jaw base corresponding to the mounting seat, the first positioning mechanism cooperates with a second positioning mechanism on the mounting seat such that positioning between the jaw assembly and the mounting seat is implemented through the first positioning mechanism and the second positioning mechanism.

3. The jaw assembly according to claim 2, wherein the connecting portion comprises: a first stationary mechanism mounted on the surface of the jaw base corresponding to the mounting seat, the first stationary mechanism cooperates with a second stationary mechanism on the mounting seat, and the first fixing mechanism and the second stationary mechanism are fixed by a third stationary mechanism to implement fixing between the jaw assembly and the mounting seat.

4. The jaw assembly according to claim 1, wherein the moving assembly comprises a sliding rail and a slider correspondingly connected to the jaw body, the sliding rail is disposed on a surface of the jaw base bearing the jaw body along a moving in or out direction of the jaw body, and the jaw body moves along the sliding rail through the slider.

5. The jaw assembly according to claim 4, wherein the sliding rail is a jaw shared sliding rail, and the jaw body moves along the jaw shared sliding rail through the slider.

6. The jaw assembly according to claim 1, wherein the jaw comprises a first jaw body, a second jaw body, a first drive apparatus, and a second drive apparatus, the first jaw body and the second jaw body are respectively connected to the jaw base through the moving assembly, the first drive apparatus is connected to the first jaw body and is configured to drive the first jaw body to move along the moving assembly, the second drive apparatus is connected to the second jaw body and is configured to drive the second jaw body to move along the moving assembly, and the first drive apparatus and the second drive apparatus are stacked along a beam transmission direction.

7. The jaw assembly according to claim 6, wherein the jaw further comprises at least one support, the at least one support is disposed on a surface of the jaw base bearing the jaw body, the first drive apparatus and the second drive apparatus are respectively connected to the at least one support, and are stacked along the beam transmission direction through the support.

8. The jaw assembly according to claim 7, wherein the first drive apparatus and/or the second drive apparatus comprise:
  a power apparatus, at least one lead screw and at least one lead screw nut;
  the lead screw nut is sleeved on the lead screw, the jaw body is connected to the lead screw nut, and the lead screw is disposed along a moving in or out direction of the jaw body; and
  an output shaft of the power apparatus is in transmission connection with the lead screw for driving the lead screw to rotate, so that the lead screw nut drives the jaw body to move along the lead screw.

9. The jaw assembly according to claim 8, wherein the first drive apparatus comprises a first power apparatus, a first lead screw and a first lead screw nut, and the second drive apparatus comprises a second power apparatus, a second lead screw, and a second lead screw nut;
  the jaw comprises a first support, a second support, and an intermediate support;
  the first support, the second support, and the intermediate support are all disposed on the surface of the jaw base bearing the jaw body, the first support and the second support are disposed oppositely, and the intermediate support is disposed between the first support and the second support;
  a first end of the first lead screw is rotatably connected to the first support, a second end of the first lead screw is rotatably connected to the intermediate support, a first end of the second lead screw is rotatably connected to the second support, a second end of the second lead screw is rotatably connected to the intermediate support, and a distance between the first lead screw and the jaw base is greater than a distance between the second lead screw and the jaw base; and
  the first power apparatus and the second power apparatus are both connected to the intermediate support, and a distance between the first power apparatus and the jaw base is greater than a distance between the second power apparatus and the jaw base, an output shaft of the first power apparatus is in transmission connection with the first lead screw, and an output shaft of the second power apparatus is in transmission connection with the second lead screw.

10. The jaw assembly according to claim 8, wherein the jaw assembly further comprises a drive pulley, a drive adapter shaft, a lead screw pulley, and a lead screw adapter shaft; and
  the drive adapter shaft is connected to the output shaft of the power apparatus, the drive pulley is connected to the drive adapter shaft, the drive pulley is in transmission connection with the lead screw pulley through a synchronous belt, the lead screw pulley is connected to the lead screw adapter shaft, and the lead screw adapter shaft is connected to the lead screw.

11. The jaw assembly according to claim 8, wherein the jaw assembly further comprises:
  a shift fork, a resistance bar slider and a resistance bar, one end of the shift fork is connected to the resistance bar slider, the other end of the shift fork is connected to the lead screw nut, the resistance bar is disposed on the surface of the jaw base bearing the jaw body, and the resistance bar slider is configured to slide along the resistance bar under drive of the lead screw nut; and
  an encoder, the encoder is connected to the power apparatus and is configured to rotate under drive of the power apparatus.

12. The jaw assembly according to claim 1, wherein the jaw assembly further comprises a first shield block disposed on a surface of the jaw base opposite to the mounting seat, the first shield block comprises a shield block through hole, and a position of the shield block through hole corresponds to a position of the beam opening.

13. The jaw assembly according to claim 12, wherein the jaw assembly further comprises a second shield block, the second shield block is connected to the jaw base and the second shield block is perpendicular to a surface of the jaw base bearing the jaw body to shield radiation at an entrance of the mounting seat of the treatment head beam shaping module of the medical accelerator.

14. The jaw assembly according to claim 1, wherein the jaw assembly further comprises a push-pull operation portion through which push and pull operations are performed, the push-pull operation portion is connected to the jaw base and perpendicular to a surface of the jaw base bearing the jaw body, and the push-pull operation portion is made of a shielding material.

15. A medical accelerator, comprising a mounting seat of a treatment head beam shaping module and a jaw assembly, the mounting seat comprising a second sliding mechanism, the jaw assembly comprising a jaw base, and a moving assembly and at least one set of jaws, each set of jaws comprising at least two jaw bodies;
  the jaw base is configured to be detachably connected to the mounting seat of the treatment head beam shaping module, and, when the jaw base is mounted on the mounting seat, a beam opening formed is located under the treatment head beam shaping module; and
  the jaw body is connected to the jaw base through the moving assembly, and the moving assembly is configured to move the jaw body to between the beam opening and the treatment head beam shaping module, or to move the jaw body out between the beam opening and the treatment head beam shaping module to adjust a beam flow through the beam opening,
  wherein the jaw base further comprises a connecting portion configured to be detachably connected to the mounting seat of the treatment head beam shaping module, the connecting portion comprises a first sliding mechanism mounted on a surface of the jaw base corresponding to the mounting seat of the treatment head beam shaping module, the first sliding mechanism is adapted to be slidable relative to the second sliding mechanism on the mounting seat of the treatment head beam shaping module such that the jaw assembly is slidable into and out of the mounting seat of the treatment head beam shaping module.

16. The medical accelerator according to claim 15, wherein a second positioning mechanism is formed on the mounting seat, and the second positioning mechanism cooperates with a first positioning mechanism formed on the jaw assembly to implement positioning between the jaw assembly and the mounting seat.

17. The medical accelerator according to claim 15, wherein a second stationary mechanism is formed on the mounting seat, and a third positioning mechanism cooperates with a first stationary mechanism formed on the jaw assembly through the second stationary mechanism to implement fixing between the jaw assembly and the mounting seat.

* * * * *